United States Patent [19]

La Marre et al.

[11] Patent Number: 4,800,235

[45] Date of Patent: Jan. 24, 1989

[54] SYNERGISTIC BIOCIDE OF 1,5-PENTANEDIAL AND A MIXTURE OF N-ALKYL DIMETHYL BENZYL AMMONIUM CHLORIDE AND N-DIALKYL METHYL BENZYL AMMONIUM CHLORIDE

[75] Inventors: Thomas M. La Marre, Aurora; Cynthia H. Martin, Plainfield, both of Ill.

[73] Assignee: Nalco Chemical Company, Naperville, Ill.

[21] Appl. No.: 873,915

[22] Filed: Jun. 13, 1986

Related U.S. Application Data

[63] Continuation-in-part of Ser. No. 770,048, Aug. 28, 1985, abandoned.

[51] Int. Cl.$^4$ ...................... A01N 33/12; A01N 35/00
[52] U.S. Cl. ...................................... 514/643; 514/705
[58] Field of Search ................................. 514/705, 643

[56] References Cited

U.S. PATENT DOCUMENTS 3,227,614  1/1966  Schever ........................... 514/643

OTHER PUBLICATIONS

Chemical Abstracts; vol. 93 (1980); #62278a; Chou et al.
*Applied Microbiology*, vol. 9, "Mixtures of Quaternary Ammonium Compounds and Long-Chain Fatty Acids as Antifungal Agents", by Kull, et al, 1961, pp. 538–541.

*Primary Examiner*—Leonard Schenkman
*Assistant Examiner*—Joseph A. Lipovsky
*Attorney, Agent, or Firm*—John G. Premo; Anthony L. Cupoli; Donald G. Epple

[57] ABSTRACT

The invention is a synergistic biocide comprising a blend of 1,5-pentanedial and a mixture of N-alkyl dimethyl benzyl ammonium chloride and N-dialkyl methyl benzyl ammonium chloride.

5 Claims, No Drawings ly discussed problems have resulted in the extensive
SYNERGISTIC BIOCIDE OF 1,5-PENTANEDIAL AND A MIXTURE OF N-ALKYL DIMETHYL BENZYL AMMONIUM CHLORIDE AND N-DIALKYL METHYL BENZYL AMMONIUM CHLORIDE This is a continuation-in-part of patent application serial No. 770,048, filed on Aug. 28, 1985, now abandoned.

INTRODUCTION

The formation of slime by microorganisms is a problem which attends many systems. For example, lagoons, lakes, ponds, poos, and such systems as cooling water systems and pump and paper mill systems, all possess conditions which are conducive to the growth and reproduction of slime-forming microorganisms. In both once-through and recirculating cooling systems, for example, which employ large quantities of water as a cooling medium, the formation of slime by microorganisms is an extensive and constant problem.

Airborne organisms are readily entrained in the water from cooling towers and find this warm medium an ideal environment for growth and multiplication. Aerobic and heliotropic organisms flourish on the tower proper while other organisms colonize and grow in such areas as the tower sump and the piping and passages of the cooling system. Such slime serves to deteriorate the tower structure in the case of wooden towers. In addition, the deposition of slime on metal surfaces promotes corrosion. Furthermore, slime carried throuh the cooling system plugs and fouls lines, valves, strainers, etc. and deposits on heat exchange surfaces. In the latter case, the impedance of heat transfer can greatly reduce the efficiency of the cooling system.

In pulp and paper mill systems, slime formed by microorganisms is also frequently and, in fact, commonly encountered. Fouling or plugging by slime also occurs in the case of pulp and paper mill systems. Of greater significance, the slime becomes entrained in the paper produced to cause breakouts on the paper machines with consequent work stoppages and the loss of production time or unsightly blemishes in the final product which result in rejects and wasted output. The previously discussed problems have resulted in the extensive utilization of biocides in cooling water and pulp and paper mill systems. Materials which have enjoyed widespread use in such applications include chlorine, organo-mercurials, chlorinated phenols, organo-bromines, and various organo-sulfur compounds. All of these compounds are generally useful for this purpose but each is attended by a variety of impediments. For example, chlorination is limited both by its specific toxicity for slime-forming organisms at economic levels and by the ability of chlorine to react which results in the expenditure of the chlorine before its full biocidal function and hazards in respect to storage, use or handling which limit their utility. To date, no one compound or type of compound has achieved a clearly established predominance in respect to the applications discussed. Likewise, lagoons, ponds, lakes, and even pools, either used for pleasure purposes or used for industrial purposes for the disposal and storage of industrial wastes, become, during the warm weather, beseiged by slime due to microorganism growth and reproduction. In the case of the recreation areas, the problem of infection, etc. is obvious. In the case of industrial storage or disposal of industrial materials, the microorganisms cause additional problems which must be eliminated prior to the materials use or the waste is treated for disposal.

Naturally, economy is a major consideration in respect to all of these biocides. Such economic considerations attach to both the cost of the biocide and the expense of its application. The cost performance index of any biocide is derived from the basic cost of the material, its effectiveness per unit of weight, the duration of its biocidal or biostatic effect in the system treated, and the ease and frequency of its addition to the system treated. To date, none of the commercially available biocides have exhibited a prolonged biocidal effect. Instead, their effectiveness is rapidly reduced as the result of exposure to physical conditions such as temperature, association with ingredients contained by the system toward which they exhibit an affinity or substantivity, etc., with a resultant restriction or elimination of their biocidal effectiveness.

As a consequence, the use of such biocides involves their continuous or frequent addition to systems to be treated and their addition to a plurality of points or zones in the systems to be treated. Accordingly, the cost of the biocide and the labor cost of such means of applying it are considerable. In other instances, the difficulty of access to the zone in which slime formation is experienced precludes the effective use of a biocide. For example, in a particular system there is no access to an area at which slime formation occurs and it may only be applied at a point which is upstream in the flow system. However, the physical or chemical conditions, e.g., chemical reactivity, thermal degradation, etc. which exist between the point at which the biocide may be added to the system and the point at which its biocidal effect is desired render the effective use of a biocide impossible.

Similarly, in a system experiencing relatively slow flow, such as a paper mill, if a biocide is added at the beginning of the system, its biocidal effect may be completely dissipated before it has reached all of the points at which this effect is desired or required. As a consequence, the biocide must be added at a plurality of points, and even then a graduated biocidal effect will be experienced between one point of addition to the system and the next point downstream at which the biocides may be added. In addition to the increased cost of utilizing and maintaining plural feed points, gross ineconomies in respect to the cost of the biocide are experienced. Specifically, at each point of addition, an excess of the biocide is added to the system in order to compensate for that portion of the biocide which will be expended in reacting with other constituents present in the system or experience physical changes which impair its biocidal activity.

The mechanisms by which chemical agents exert antimicrobial activity depend upon the effective contact between the chemical and microorganism and involve disruptive interaction with a biochemical or physical component of the organism, which component is essential to its structure of metabolism. The targets may be an enzyme, or enzymes, the cell membrane, intracellular systems, the cytoplasm, or combination of these; and the nature of the action is dependent on the organism, on the antimicrobial agent, and on the environment in which the interaction occurs. 1,5-pentanedial, for example, often acts through the alkylation of amino and sulfhydryl groups of proteins. Cationic surface active compounds, such as the quaternary ammonium compounds, form electrostatic bonds with carboxyl groups in proteins and enzymes that interfere with oxidation-reduction and other biochemical reactions. The cell wall is damaged, lysis occurs, and metabolites leak out of the cell. N-alkyl dimethyl benzyl ammonium chloride, N-dialkyl methyl benzyl ammonium chloride, and 1,5-pentanedial are powerful toxicants to bacteria, algae, and fungi at low concentrations, as low as 1–10 ppm of active toxicant; 1,5-pentanedial is particularly sporicidal as well.

The present invention relates to the use of a blend of N-alkyl dimethyl benzyl ammonium chloride and N-dialkyl methyl benzyl ammonium chloride in combination with the toxicant, 1,5-pentanedial, to provide superior antimicrobial activity through a synergy in which the disruptive interaction on the organism by the two toxicants together is greater than the sum of both toxicants taken alone. The snergy does not arise from an unexpected additivity of the components or from a predictable improvement in activity. In all cases, the synergism depends largely on the interactions of the antimicrobial agents with the organism, the cellular processes of this latter being so complex in these interactions as to render such synergism an unpredictable, and indeed rare, phenomenon.

THE INVENTION

A synergistic biocidal composition useful in treating industrial process waters to prevent the growth of microorganisms which comprises from 10–90% by weight of 1,5-pentanedial and from 90–10% by weight of a mixture comprising:

(a) N-alkyl dimethyl benzyl ammonium chloride and
(b) N-dialkyl methyl benzyl ammonium chloride, wherein the ratio of (a) to (b) is within the range of 10:1 to 1:10 and the alkyl group contains between 12–20 carbon atoms in chain length.

The troublesome slime forming bacteria in industrial process waters tend to be primarily gram-negative rod-shaped aerobes. Of this group, *Pseudomonas aeruginosa* is one of the most common and most difficult to control. The invention is capable of affording good control of *Pseudomonas aeruginosa*. It is also capable of affording control of other species of bacteria, in particular other species of gram-negative, rod-shaped aerobes of such genera as Aerobacter, Flavobacterium, Pseudomonas, particularly, *Pseudomonas aeruginosa, Pseudomonas fluorescens, Pseudomonas levanicum, Pseudomonas stutzeri, Pseudomonas maltophilia, Aerobacter aerogenes, Aerobacter cloacae.*

Similarly the fungi, *Aspergillus niger*, is one of the most common species of mold in process waters and one of the most difficult to control. *Saccharomyces cerevisiae* is a common yeast. This invention is capable of affording control of *Aspergillus niger* and *Saccharomyces cerevisiae* and other species of fungi which are common in process waters, species in such genera as Aspergillus, Monilia, as well as *Aspergillus fumigatus, Aspergillus niger, Penicillium chrysogenum, Monilia candida, Geotrichum candidum,* and *Saccharomyces cerevisiae.*

While the two biocides may be combined in the weight ratios shown above when they are combined to treat fungi and, in particular, either *Asperigillus niger* or *Saccharomyces cerevisiae*, they are highly synergistic with the weight percent of tributyl tetradecyl phosphonium chloride and the weight percent of methylene bis thiocyanate ranges between 10–90% by weight of 1,5 pentanedial and from 90–10% by weight of a mixture comprising:

(a) N-alkyl dimethyl benzyl ammonium chloride and
(b) N-dialkyl methyl benzyl ammonium chloride, wherein the ratio of (a) to (b) is within the range of 10:1 to 1:10 and the alkyl group contains between 12–20 carbon atoms in chain length.

Thus, the invention is not only effective in providing improved synergistic biocidal compositions, but it also comprises the utilization of these compositions in treating industrial process waters of the types previously described.

The Mixed Alkyl Methyl Benzyl Ammonium Chlorides

It is well known that blends of
(a) N-alkyl dimethyl benzyl ammonium chloride and
(b) N-dialkyl methyl benzyl ammonium chloride provide a superior biocide. As indicated above, the alkyl group may vary between $C_{12}$–$C_{20}$. It is preferred that the alkyl group be composed primarily of a mixed alkyl group in which $C_{14}$–$C_{16}$ alkyl groups predominate. Such mixed alkyl groups are derived from animal fats or vegetable oils or they may be obtained from certain petroleum fractions. The alkyl groups may be either straight chained or branched. In a preferred embodiment of the invention, the weight ratio of (a) to (b) is about 8:1. A commercial embodiment containing a mixture of (a) and (b) contains 26.9% by weight of (a), 5.1% by weight of (b), with the balance of the product being water of dilution. This particular product contains an alkyl group distribution of 60% $C_{14}$, 30% $C_{16}$, 5% $C_{12}$, and 5% $C_{18}$.

Evaluation of the Invention

The synergism of these two components is demonstrated by adding 1,5-pentanedial (PD) and a mixture of N-alkyl dimethyl benzyl ammonium chloride and N-dialkyl methyl benzyl ammonium chloride (BAC) in varying ratios over a range of concentrations to sterile white water from a paper mill. The white water, adjusted to the desired pH, was inoculated with *Pseudomonas aeruginosa*, ATCC 15442. The total count of the control was $1.0 \times 10^7$ bacteria per millimeter. The concentrations of the above toxicants were added to aliquots of the inoculated white water, and these aliquots were incubated at 37° C. for 24 hours. In this study of the control of bacterial growth, the nutrient medium for plating was tryptone glucose extract agar, poured at 50° C. into sterile Petri dishes containing the appropriate dilution of the white water which had been inoculated and treated as described. Once the medium in these dilution plates had solidified, the plates were incubated for over forty-eight hours at 37° C. After the incubation, the results were read as growth or no growth. The lowest concentration of each toxicant or of each ratio of the combined toxicants that prevented growth on the agar was taken as the end point. This procedure provides the oxicant with a greater challenge by testing the toxicants under conditions which approximate the conditions under which they will be used.

The test against fungi followed the same procedure with these exceptions. The white water was inoculated with *Aspergillus niger* and *Saccharomyces cerevisiae* to a count of $2.2 \times 10^5$ fungi per milliliter. The aliquots of inoculated and treated white water were incubated at 30° C. for 5 days. The medium used for plating was potato dextrose agar, acidified with tartaric acid to a pH of 4.5. The plates were incubated 5 days at 30° C.

The end points of each of the ratios tested were compared with end points of the concentrations of the pure toxicants. Synergism was determined according to the industrially-accepted method described by S. C. Kull, P. C. Eisman, H. D. Sylwestrowicz, and R. L. Mayer in *Applied Microbiology*, Vol. 9, pages 538-541, (1936), which is herein included as reference.

As regards the Kull, et al. document, the data here presented can be described as follows:

$Q_A$ = the ppm of actives of BAC alone which produced an end-point.
$Q_a$ = the ppm of actives of BAC, in combination which produced an endpoint.
$Q_B$ = the ppm of actives of 1,5-pentanedial alone which produced an endpoint.
$Q_b$ = the ppm of actives of 1,5-pentanedial, in combination, which produced an end point.

if $\dfrac{Q_a}{Q_A} + \dfrac{Q_b}{Q_B} < 1$ indicates synergy

> 1 indicates antagonisum

= 1 indicates additvity

Ratio of BAC/PD: 100/0, 0/100, 90/10, 10/90, 75/25, 25/75, 50/50.

The above test method is reproduceable and is a good method for determining the range of synergism existing against candidate biocides being screened for application in the treatment of biologically contaminated industrial waters. The efficacy and validity of this test method is discussed in the Appendix which appears hereafter. For purposes of simplification of test results presented hereafter, the Appendix also contains the calculations used to produce the test results set forth in Tables I and II. The effectiveness of the combination of 1,5 pantanedial, N-alkyl dimethyl benzyl ammonium chloride and N-dialkyl methyl benzyl ammonium chloride is set forth in Tables I and II.

TABLE I

SYNERGISM STUDY FOR COMBINATION
BIOCIDES AGAINST FUNGI
+: <90% reduction in organisms
−: >90% reduction in organisms
Control Culture: 2.2 × 10⁵ organisms per ml

| Ratio[1] Comp. A[2]/ Comp. B[3] | 0 | 5 | 7.5 | 10 | 20 | 30 | 40 | 50 | 60 | 70 | 80 | 90 | 100 |
|---|---|---|---|---|---|---|---|---|---|---|---|---|---|
| 100/0* | + | + | + | + | + | + | + | + | + | + | + | + | + |
| 0/100 | + | + | + | + | + | + | + | + | − | − | − | − | − |
| 90/10 | + | − | − | − | − | − | − | − | − | − | − | − | − |
| 10/90 | + | + | + | − | − | − | − | − | − | − | − | − | − |
| 75/25 | + | + | − | − | − | − | − | − | − | − | − | − | − |
| 25/75 | + | − | − | − | − | − | − | − | − | − | − | − | − |
| 50/50 | + | + | − | − | − | − | − | − | − | − | − | − | − |

| Ratio Comp. A/Comp. B | $\dfrac{Qa + Qb}{QA + QB}$ | Rating |
|---|---|---|
| 90/10 | <0.0128 | <1 Synergy |
| 10/90 | <0.302 | <1 Synergy |
| 75/25 | <0.0369 | <1 Synergy |
| 25/75 | <0.0638 | <1 Synergy |
| 50/50 | <0.0663 | <1 Synergy |

*100/0 does not show a 90% reduction even at concentrations greater than 1000 ppm active
[1]Based on active ingredients.
[2]1,5-Pentanedial
[3]A mixture of N—alkyl dimethyl benzyl ammonium chloride & N—dialkyl methyl benzyl ammonium chloride

TABLE II

SYNERGISM STUDY FOR COMBINATION
BIOCIDES AGAINST BACTERIA
Growth: +    No Growth: −
Control Culture: 1 × 10⁷ organisms per ml

| Ratio Comp. A/ Comp. B | .3 | .6 | 1.0 | 1.5 | 3.0 | 5.0 | 7.5 | 10 | 20 | 30 | 40 | 50 | 60 |
|---|---|---|---|---|---|---|---|---|---|---|---|---|---|
| 100/0 | + | + | + | + | + | + | + | + | + | + | + | + | − |
| 0/100 | + | + | + | + | + | + | + | + | + | + | − | − | − |
| 90/10 | + | + | + | + | + | + | + | + | − | − | − | − | − |
| 10/90 | + | + | + | + | + | + | + | + | + | − | − | − | − |
| 75/25 | + | + | + | + | + | + | + | + | + | − | − | − | − |
| 25/75 | + | + | + | + | + | + | + | + | + | − | − | − | − |
| 50/50 | + | + | + | + | + | + | + | + | + | − | − | − | − |

| Ratio Comp. A/Comp. B | $\dfrac{Qa + Qb}{QA + QB}$ | Rating |
|---|---|---|
| 90/10 | 0.350 | <1 Synergy |
| 10/90 | 0.725 | <1 Synergy |
| 75/25 | 0.375 | <1 Synergy |
| 25/75 | 0.688 | <1 Synergy |
| 50/50 | 0.625 | <1 Synergy |

ANTAGONISTIC COMBINATIONS

Using the same method employed to determine the synergy of the two toxicants presented in this invention, the same two toxicants were proved to be antagonistic, or at best additive, in combination with other toxicants. Three examples are given below:

First, 1,4-pentanedial (Composition A) was found to be antagonistic in combination with an amine, 1-alkyl ($C_6$–$C_{18}$)amino-3-aminopropane monoacetate (Composition C).

| Ratio (Comp. A/ Comp. C) | Endpoints (ppm Actives) | $\dfrac{Qa}{QA} + \dfrac{Qb}{QB}$ | Ratings |
|---|---|---|---|
| 100/0 | 130 | | All Ratios are additive or antagonistic. |
| 0/100 | 80 | | |
| 90/10 | 120 | 0.981 | |
| 10/90 | 80 | 0.962 | |
| 75/25 | 120 | 1.067 | |
| 25/75 | 100 | 1.130 | |
| 50/50 | 100 | 1.010 | |

Second, 1,5-pentanedial (Composition A) was also found to be antagonistic in combination with 2-(thiocyanomethylthio) benzothiazole (Composition D).

| Ratio (Comp. A/ Comp. C) | Endpoints (ppm Actives) | $\dfrac{Qa}{QA} + \dfrac{Qb}{QB}$ | Ratings |
|---|---|---|---|
| 100/0 | 130 | | |
| 0/100 | 90 | | |
| 90/10 | 140 | 1.125 | Antagonistic |
| 10/90 | 100 | 1.076 | Antagonistic or Additive |
| 75/25 | 110 | 0.941 | Additive |
| 25/75 | 120 | 1.231 | Antagonistic |
| 50/50 | 120 | 1.129 | Antagonistic |

Third, the blend of quaternary amines (Composition B) used in this invention was found to be antagonistic in combination with 2-(p-hydroxyphenol)-glyoxylohydroximoyl chloride (Composition E).

| Ratio (Comp. A/ Comp. C) | Endpoints (ppm Actives) | $\frac{Qa}{QA} + \frac{Qb}{QB}$ | Ratings |
|---|---|---|---|
| 100/0 | 20 | | |
| 0/100 | 30 | | |
| 90/10 | 40 | 1.933 | Antagonistic |
| 10/90 | 20 | 0.700 | Synergistic |
| 75/25 | 60 | 2.750 | Antagonistic |
| 25/75 | 30 | 1.125 | Antagonistic |
| 50/50 | 70 | 2.917 | Antagonistic |

APPENDIX
DISCUSSION

The conventional presentation of a test of synergy demands that the data be presented in terms of growth or no growth. The convention has the merit of presenting the data simply and directly in terms that make the calculation of synergy straightforward. This presentation may, however, require a thorough explanation of the factors which are taken into account in the determination of the endpoints of the test. The determination of synergy depends wholly on these endpoints.

The data presented in Table I show that the invention is synergistic in effect against fungi. The control contained both molds and yeasts to a total count of $2.2 \times 10^5$ organisms per ml. The data are given in terms of a 90% reduction in the total count, for two reasons. First, a 90% or one-log reduction represents excellent activity for the invention as it would be applied in Industrial process waters. Second, the 90% reduction is quite significant in the case of molds; a complete kill of the molds would be difficult to achieve, and the endpoints for a 100% reduction are frequently unclear. In any case, the endpoints in Table I unquestionably show synergy; any interpretation of the data confirms the synergy: the ratios are nearly ten times more effective than the toxicants alone.

The data in Table II also demonstrate synergy, but may require more explanation. First, the indication of growth (+) in Table II is heavy growth. No growth (−) indicates no growth on a zero-dilution plate, on a one-dilution plate, and on a two-dilution plate. The zero-dilution plate will show as few as one bacterial colony per milliliter; the lowest count on one-dilution plate is ten bacteria per milliliter, and the two-dilution plate shows a bacterial count greater than $10^2$ bacteria per milliliter. In short, in Table II, the difference between growth (+) and no growth (−) involves a three-log reduction in bacterial count. For example, in the case of the ratio 100/0, the bacterial count at concentration of 50 ppm was greater than $10^2$ bacteria per milliliter. At 60 ppm, the bacterial count was below detection (1 bacteria per milliliter). Therefore, the endpoint for 100/0 is taken to be 60 ppm.

The endpoint for 100/0 is, in the strictest sense, between 50 and 60 ppm. In this case, where a concentration of toxicant as high as 50 ppm is not capable of completely inhibiting growth, a three-log reduction in bacterial count is not to be expected by increasing the concentration of biocide by 1-5 ppm. The endpoint cannot fall closer to 50 ppm than to 60 ppm. The 10 ppm is indeed significant when testing toxicants with this magnitude of toxicity. Additional data points at closer intervals are unnecessary. The progression of the increments between concentrations in these experiments (0.3, 0.6, 1.0, 1.5, 3.0, 5.0, 7.5, 10, 20 . . . etc.) is standard method in producing representation microbiological data.

The same logic applies to all the endpoints of the test. The best and worst extrapolations of the data can be determined in this way. Let us say, for the ratios 100/0 and 0/100, that;

$$55 < QA < 60$$

$$35 < QB < 40$$

Let us use the ratio 10/90 in this example because it is the least synergistic of the ratios. As described above, the endpoint for 10/90 must fall closer to 30 than to 20, therefore the endpoint can be described thus:

$$25 > 10/90 < 30$$

In the worst possible case;

$$QA = 55$$

$$QB = 35$$

And the worst endpoint for 10/90 under these circumstances is 30 ppm. Therefore, $$Qa = 0.1 \times 30 = 3$$

$$QB = 0.9 \times 30 = 27$$

The formula for the calculation of synergy is defined to be;

$$\frac{Qa}{QA} + \frac{Qb}{QB} = 0.825$$

This formula shows the extent to which the combination of the two toxicants creates a surprising increase in activity. When the synergy ratio is less than 1, the combination is truly synergistic instead of antagonistic or merely additive. In this experiment, calculating the worst possible case for the least effective ratio, the ratio is still clearly synergistic.

A table can be made showing the best and worst cases for the data presented in Table II.

| Ratio (Comp. A. Comp. B | Synergy Ratio | |
|---|---|---|
| | Best Case | Worst Case |
| 90/10 | 0.263 | 0.384 |
| 10/90 | 0.604 | 0.825 |
| 75/25 | 0.281 | 0.415 |
| 25/75 | 0.573 | 0.778 |
| 50/50 | 0.521 | 0.701 |

Even in the worst possible cases, the results still indicate synergy. This presentation of the data goes to show how truly representative the endpoints are. The data, as presented and calculated in Table II, are not extrapolated into the best or worst cases. Instead, the data summarize the activity tested using standard method. As mentioned above, this interpretation also depends on understanding that the difference between growth and no growth in the synergy study against bacteria involves a three-log reduction in bacteria count. These interpretations of the data confirm that each combination of toxicants results in an unexpected amelioration of toxicity.

| Calculations for TABLE I | |
|---|---|
| $Q_A = >1000$ ppm active Comp. A $Q_B = 60$ ppm active Comp. B | $\dfrac{Q_a}{Q_A} + \dfrac{Q_b}{Q_B} < 1 =$ Synergy |

A. 90/10
$Q_a = 5.0$ ppm × .90 = 4.5
$Q_b = 5.0$ ppm × .10 = 0.5

$$\dfrac{4.5}{>1000} + \dfrac{0.5}{60} = 0.0128$$

B. 10/90
$Q_a = 10$ ppm × .10 = .2
$Q_b = 10$ ppm × .90 = .18

$$\dfrac{.2}{>1000} + \dfrac{.18}{60} = 0.302$$

C. 75/25
$Q_a = 7.5$ ppm × 0.75 = 5.625
$Q_b = 7.5$ ppm × 0.25 = 1.895

$$\dfrac{5.625}{>1000} + \dfrac{1.875}{60} = 0.0369$$

D. 25/75
$Q_a = 5$ ppm × 0.25 = 1.25
$Q_b = 5$ ppm × 0.75 = 3.75

$$\dfrac{1.25}{>1000} + \dfrac{3.75}{60} = 0.0638$$

E. 50/50
$Q_a = 7.5$ ppm × 0.50 = 3.75
$Q_b = 7.5$ ppm × 0.50 = 3.75

$$\dfrac{3.75}{>1000} + \dfrac{3.75}{60} = 0.0663$$

| Calculations for TABLE II | |
|---|---|
| $Q_A = 60$ ppm active Comp. A $Q_B = 40$ ppm active Comp. B | $\dfrac{Q_a}{Q_A} + \dfrac{Q_b}{Q_B} < 1 =$ Synergy |

A. 90/10
$Q_a = 20$ ppm × .90 = 18
$Q_b = 20$ ppm × .10 = 2

$$\dfrac{18}{60} + \dfrac{2}{40} = 0.350$$

B. 10/90
$Q_a = 30$ ppm × .10 = 3
$Q_b = 30$ ppm × .90 = 27

$$\dfrac{3}{60} + \dfrac{27}{40} = 0.725$$

C. 75/25
$Q_a = 20$ ppm × 0.75 = 15
$Q_b = 20$ ppm × 0.25 = 5

$$\dfrac{15}{60} + \dfrac{5}{40} = 0.375$$

D. 25/75
$Q_a = 30$ ppm × 0.25 = 7.5
$Q_b = 30$ ppm × 0.75 = 22.5

$$\dfrac{7.5}{60} + \dfrac{22.5}{40} = 0.688$$

E. 50/50
$Q_a = 0\ 30$ ppm × 0.50 = 15
$Q_b = 0\ 30$ ppm × 0.50 = 15

$$\dfrac{15}{60} + \dfrac{15}{40} = 0.625$$

We claim:

1. A synergistic biocidal composition useful in treating industrial process waters to prevent the growth of gram-negative bacteria and fungi which comprises from 10–90% by weight of 1,5-pentanedial and from 90–10% by weight of a mixture comprising:
   (a) N-alkyl dimethyl benzyl ammonium chloride and
   (b) N-dialkyl methyl benzyl ammonium chloride, wherein the ratio of (a) to (b) is within the range of 10:1 to 1:10 and the alkyl group contains between 12–20 carbon atoms in chain length.

2. The synergistic biocidal composition of claim 1 wherein the ratio of (a) to (b) is about 6:1 and the alkyl groups are predominantly composed of $C_{14}$–$C_{16}$ alkyl groups.

3. A method of controlling the growth of gram-negative bacteria and fungi of the type commonly found in industrial process waters which comprises treating said waters with a biocidal amount of the composition of claim 1 or 2

4. A method for controlling the growth of Pseudomonas bacteria which comprises treating said waters with a biocidal amount of the composition of claim 1 or 2.

5. A method for controlling the growth of fungi from the group consisting of Saccharomyces yeast and Aspergillus molds which comprises treating said waters with a biocidal amount of the composition of claim 1 or 2.

* * * * *